(12) United States Patent
Engel et al.

(10) Patent No.: US 6,805,733 B2
(45) Date of Patent: Oct. 19, 2004

(54) OUTWARDLY PROJECTING AIR PURIFIER

(75) Inventors: Stuart Engel, Côte St.Luc (CA); Normand Brais, Rosemére (CA); Marc Lupien, Montréal (CA)

(73) Assignee: Sanuvox Technologies, Montreal (CA)

( * ) Notice: Subject to any disclaimer, the term of this patent is extended or adjusted under 35 U.S.C. 154(b) by 0 days.

(21) Appl. No.: 10/307,455

(22) Filed: Dec. 2, 2002

(65) Prior Publication Data

US 2003/0131734 A1 Jul. 17, 2003

(30) Foreign Application Priority Data

Dec. 14, 2001 (CA) ............................................. 2365148

(51) Int. Cl.[7] ................................................ A61L 9/20
(52) U.S. Cl. ...................... 96/224; 250/436; 250/438; 422/24; 422/121
(58) Field of Search ...................... 96/224, 16; 422/24, 422/121; 250/436, 438

(56) References Cited

U.S. PATENT DOCUMENTS

| | | | | |
|---|---|---|---|---|
| 2,332,663 A | * | 10/1943 | Olson | 422/121 |
| 3,107,974 A | * | 10/1963 | Potapenko | 96/224 X |
| 3,246,144 A | * | 4/1966 | Beall et al. | 422/24 X |
| 3,313,971 A | * | 4/1967 | Nagy | 96/224 X |
| 3,403,252 A | * | 9/1968 | Nagy | 96/224 X |
| 3,518,046 A | * | 6/1970 | Cicirello | 96/224 X |
| 4,210,429 A | * | 7/1980 | Golstein | 422/121 X |
| 5,380,503 A | * | 1/1995 | Fujii et al. | 422/121 X |
| 5,616,172 A | * | 4/1997 | Tuckerman et al. | 96/16 |
| 5,753,106 A | * | 5/1998 | Schenck | 250/436 X |
| 5,879,435 A | * | 3/1999 | Satyapal et al. | 422/24 X |
| 5,891,399 A | * | 4/1999 | Owesen | 422/121 |
| 6,221,314 B1 | * | 4/2001 | Bigelow | 422/24 |
| 6,228,327 B1 | * | 5/2001 | Matschke | 250/436 X |
| 6,337,483 B1 | * | 1/2002 | Matschke | 250/436 X |
| 2003/0021721 A1 | * | 1/2003 | Hall | 96/224 X |

FOREIGN PATENT DOCUMENTS

JP          63-194794      * 11/1988    .................. 422/24

* cited by examiner

Primary Examiner—Richard L. Chiesa
(74) Attorney, Agent, or Firm—Lorusso Loud & Kelly LLP; Marc Lupien

(57) ABSTRACT

An outwardly projecting air purifier including a support, a generally cylindrical array of UV lamp assemblies mounted to the support, wherein each UV lamp assembly includes a reflector having a generally parabolic inner surface and a UV lamp so mounted to the reflector that the inner surface of the reflector reflects a portion of the ultraviolet radiation emitted by the lamp in an outward, radial, direction is described herein. The air purifier also includes a convex shaped deflector element so mounted to the support that the airflow is deflected by the deflector element and brought near the lamps.

30 Claims, 8 Drawing Sheets

FIG_5

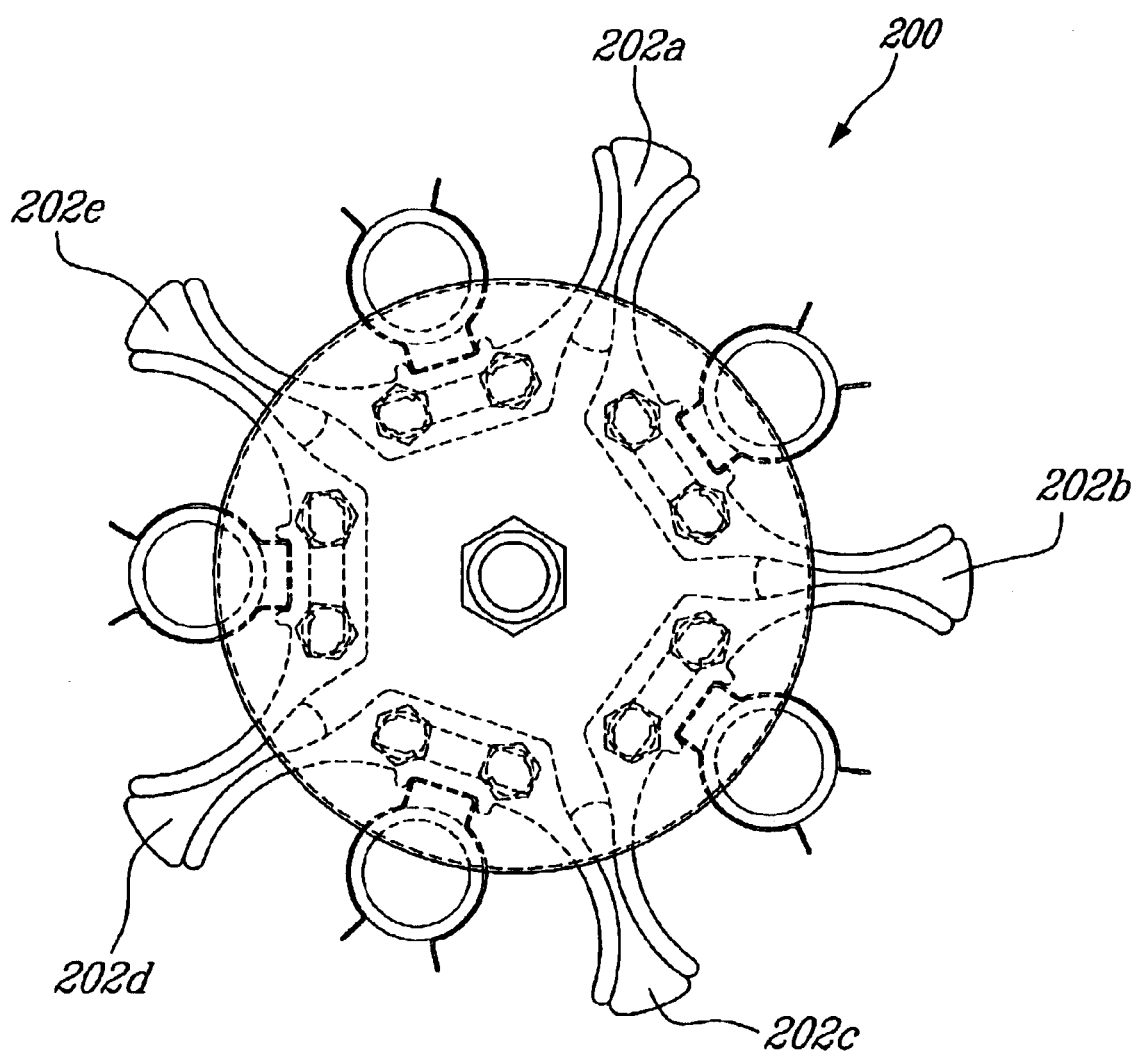
FIG_7

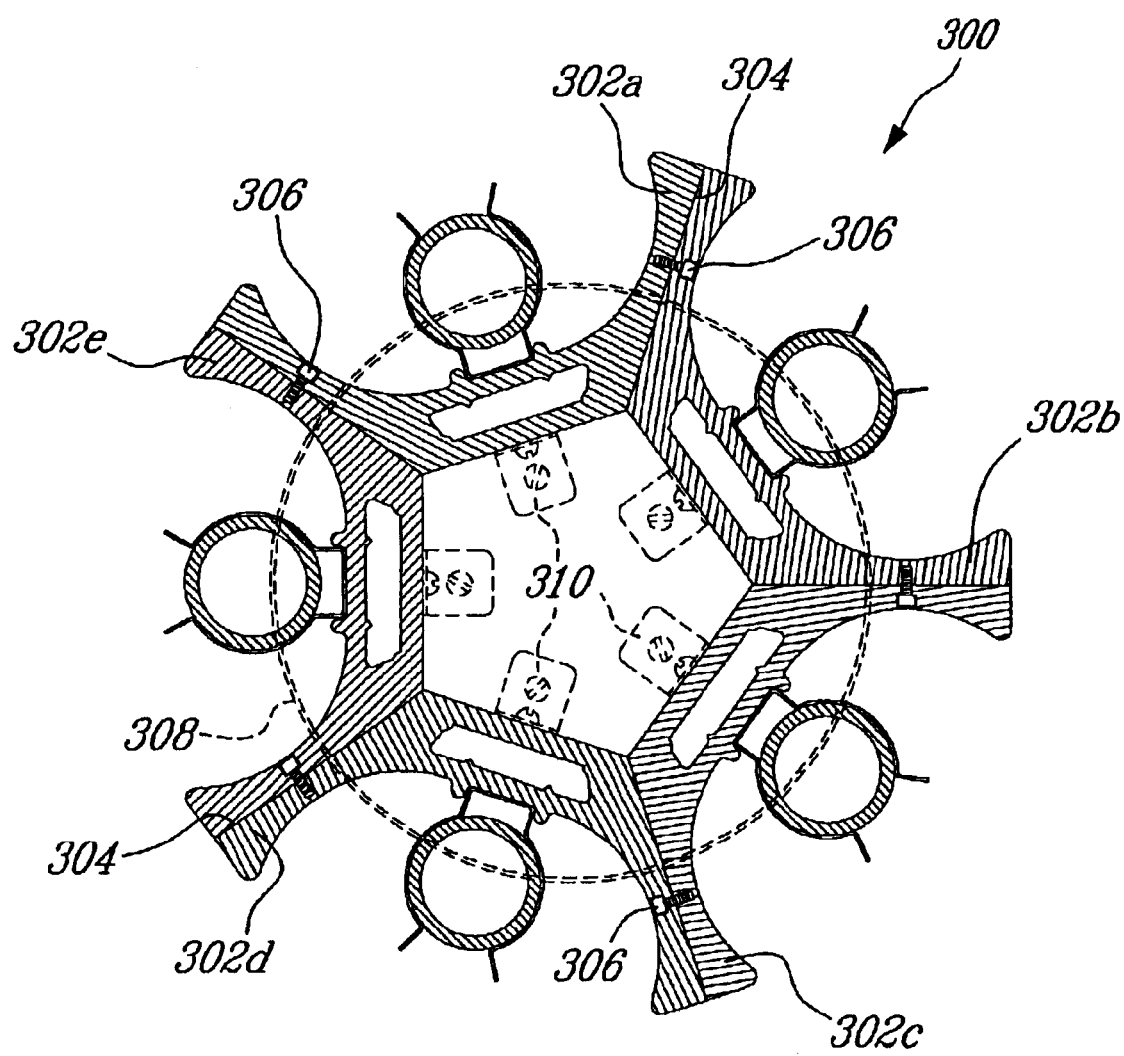
FIG_8

OUTWARDLY PROJECTING AIR PURIFIER

FIELD OF THE INVENTION

The present invention relates to air purifiers. More specifically, the present invention is concerned with an outwardly projecting air purifier comprising an assembly of UV lamps and reflector, allowing the air purifier to be used in air ducts and in other types of ventilation systems.

BACKGROUND OF THE INVENTION

Indoor Air Quality related problems, often referred to as "SICK BUILDING SYNDROMES", costs the North American economy well over 100 billion dollars each year in health care, absenteeism, lost production time and lost revenue. This problem is compounded by the "Anthrax scare", since anthrax spores (structures whose role is propagation) can be readily transported through the ventilation system of a building.

The human immune system often responds violently when exposed to toxins released by bacteria and molds in ventilation systems, and displays systems commonly called allergies. The microorganisms found in buildings are viruses, bacteria and their components such as endotoxins, and fungi and their metabolic products such as mycotoxins and antigens.

Most environments contain a large variety of bacteria. Health risks increase only when the pathogen bacteria concentration is permitted to amplify in an indoor environment, and these organisms or their by-products become airborne. Legionnaire's disease, some pneumonias, anthrax, and tuberculosis are airborne infectious diseases caused by bacteria.

Anthrax is an acute infectious disease caused by the spore-forming bacterium *Bacillus anthracis*. It is most commonly found in hoofed animals but can also infect humans. The serious forms of human anthrax are inhalation anthrax (often fatal), cutaneous anthrax, and intestinal anthrax. In October 2001, four workers died from inhalation anthrax and an additional 13 developed cutaneous or inhalation disease as a result of intentional terrorist activity. Employers and workers are concerned about possible exposure to *Bacillus anthracis* in the workplace.

Endotoxins are components of a bacterial cell. More precisely, they are components of the outer membrane of some bacteria. Dangerous levels of airborne endotoxins have been reported in numerous work environments, including offices and laboratories. They can cause fever and malaise, changes in white blood cell counts, and respiratory and gastrointestinal problems.

There are over 100 000 known species of fungi. Microscopic fungi include yeasts and molds. Most fungi produce spores that are carried by the air. The diameter of these spores varies from approximately 1 to 60 microns. Most substances containing carbon, abundant in indoor and outdoor environments, can serve as nutrients for molds. Accumulation of humidity in the indoor environment is the most important factor to be controlled to limit fungal growth.

Some fungi can invade living cells, causing infectious diseases. Several molds produce proteins and glycoproteins that are highly antigenic i.e. capable of producing an immune response, and can cause hypersensitivity diseases or allergies in susceptible individuals. Practically all living organisms contain proteins, glycoproteins and polysaccharides with antigenic potential. Growing molds may additionally produce several volatile organic compounds, some of which are at the origin of the frequently observed characteristic moldy odor.

Of all the hyper sensibility diseases, only hypersensitivity pneumonitis allergic asthma, allergic rhinitis and allergic aspergillosis are known as resulting from exposure to airborne antigens.

Water reservoirs and air conditioning units cooling coils where warm water condenses are good growth media for various bacteria fungi or protozoa. Consequently, ventilation system components, particularly some types of humidifiers, can aerosolize droplets from water reservoirs and are therefore of special interest. Hypersensitivity pneumonitis has occurred in individuals when building humidification systems were contaminated.

It is now common knowledge that the energy efficient designs of the 1970's resulted in the construction of tighter building envelopes having improved insulation, low energy consuming ventilation and having no operable windows. These designs have contributed to an increase in indoor pollutant sources, since these pollutants are no longer sufficiently diluted with fresh air. Additionally, new building materials, products, and furnishing emit a significant number of hazardous chemicals into the air. The resulting situation results in an increase in contaminants circulating through the indoor environment, with insufficient outside air being introduced to dilute these contaminants.

Indoor air quality (IAQ), is a complex issue, much more so than any single environmental issue. There are hundreds of pollutants that effect IAQ and thousands of sources. Research reveals that more than 900 different contaminants are present in indoor environments.

If needs for comfort, health and well-being are not satisfied, building occupants may begin to complain of symptoms which are associated with poor IAQ. Headaches, burning and itching eyes, respiratory difficulties, skin irritation, nausea, congestion, cough, sneezing, and fatigue are some of the more frequent complaints. Complaints of funny odors in the air are usually indicative of poor air quality.

An increasing percentage of the population is becoming more sensitive to a number of chemicals in indoor air, each of which may occur at very low concentrations. The existence of this condition has been identified as "Multiple Chemical sensitivity" (MCS) and is currently the subject of chemical research.

According to the EPA, the effects of IAQ problems are often non-specific symptoms rather than clearly defined illnesses. Although they can be vague, the symptoms seem generally worse after a day in the building (office or work place) and may altogether disappear when the occupant leaves the building.

In light of these problems, the importance of efficiently purified air, rid of biological contaminants, becomes readily understandable.

OBJECTS OF THE INVENTION

An object of the present invention is to provide an outwardly projecting air purifier.

SUMMARY OF THE INVENTION

More specifically, according to an embodiment of the present invention, there is provided an outwardly projecting air purifier to be used in an air duct supporting a longitudinal airflow and comprising:

a support to be positioned within the air duct;

a plurality of UV lamp assemblies longitudinally mounted to said support; each of said UV lamp assemblies including a reflector having a generally parabolic inner surface and a UV lamp so mounted to said reflector that said generally parabolic inner surface reflects UV radiation emitted by said UV lamp in a radial direction; and a convex deflector element so mounted to said support that the airflow is deflected over said UV lamp assemblies.

According to another aspect of the present invention, there is provided an outwardly projecting air purifier to be positioned longitudinally within an air duct supporting an airflow comprising:

a support;

a convex shaped deflector element so mounted to said support as to be located upstream with respect to the airflow;

at least two reflectors having a generally parabolic inner surface mounted to said support; and at least two UV lamps each being so mounted to a corresponding reflector that UV radiation emitted by said lamps is reflected in a radial direction;

wherein each of said at least two reflectors is so mounted to said support that airflow is deflected by said convex shaped deflector element over said UV lamps.

According to a third aspect of the present invention, there is provided an outwardly projecting air purifier to be used in an air duct supporting a longitudinal airflow and comprising:

a plurality of adjacently interconnected UV lamp assemblies each including:

a reflector having a generally parabolic inner surface and an outer surface so configured as to be interconnectable with the outer surface of a reflector of an adjacent UV lamp assembly; and a UV lamp so mounted to said reflector that said generally parabolic inner surface reflects UV radiation emitted by said UV lamp in a radial direction;

a convex deflector element so mounted to said reflectors that the airflow is deflected over said UV lamp assemblies.

It is to be noted that the expression "air duct" is to be construed in the present description and appended claims as meaning any passage designed to guide ventilating air.

It is to be noted that the expression "plurality" is to be construed in the present description and appended claims as meaning at least two.

It is to be noted that the expression "generally parabolic" is to be construed in the present description and appended claims as meaning a generally concave cross-section that would adequately reflect incident radiation thereon in a generally radial direction.

Other objects, advantages and features of the present invention will become more apparent upon reading of the following non-restrictive description of preferred embodiments thereof, given by way of example only with reference to the accompanying drawings.

BRIEF DESCRIPTION OF THE DRAWINGS

In the appended drawings:

FIG. 7 is an end view similar to FIG. 2 but illustrating an outwardly projecting air purifier according to a third embodiment of the present invention; and FIG. 8 is an end view similar to FIG. 2 but illustrating an outwardly projecting air purifier according to a fourth embodiment of the present invention.

DESCRIPTION OF AN EMBODIMENT OF THE INVENTION

Figure 1:
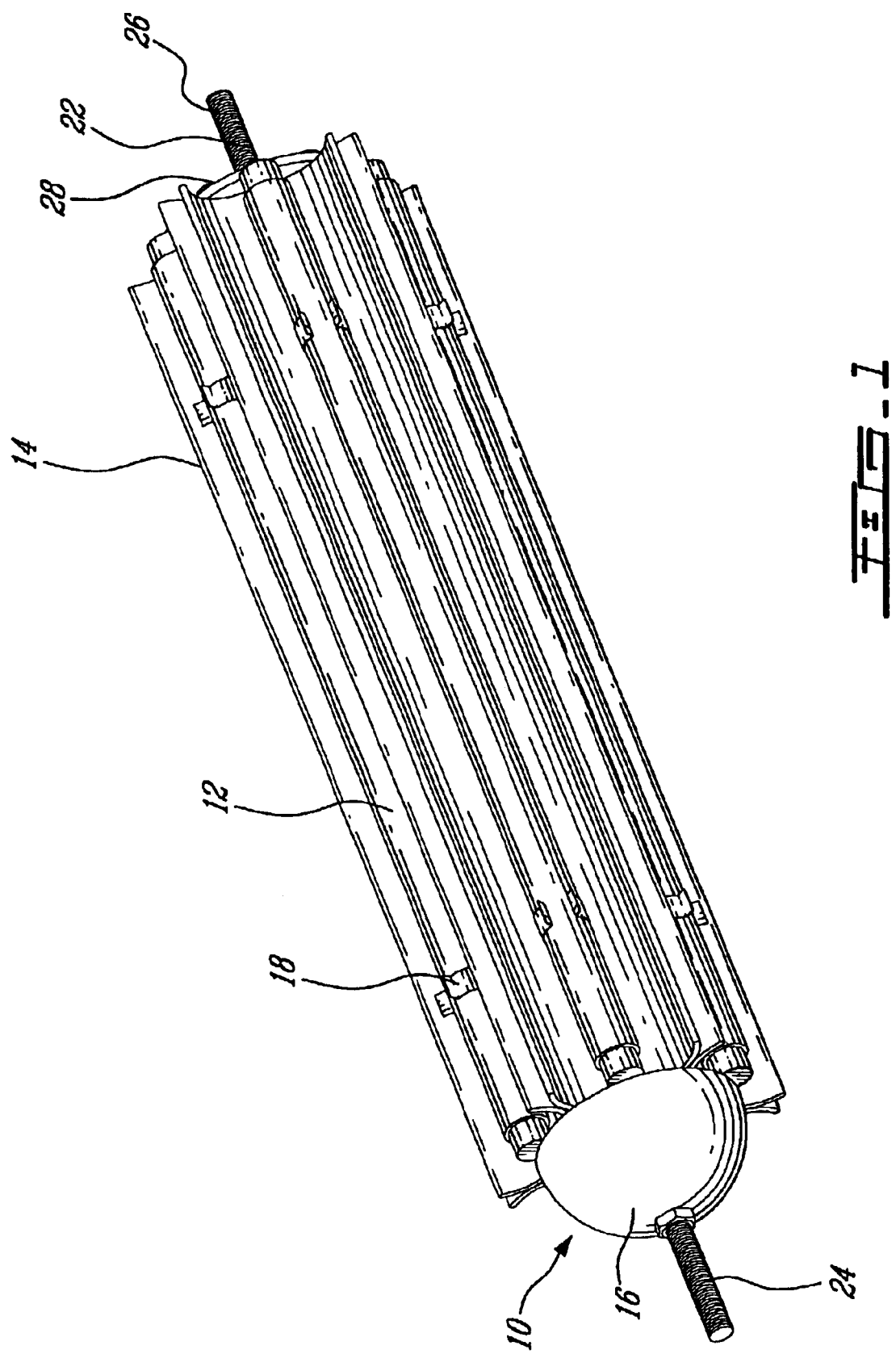
FIG. 1 is a perspective view illustrating an outwardly projecting air purifier according to an embodiment of the present invention.
Figure 2:
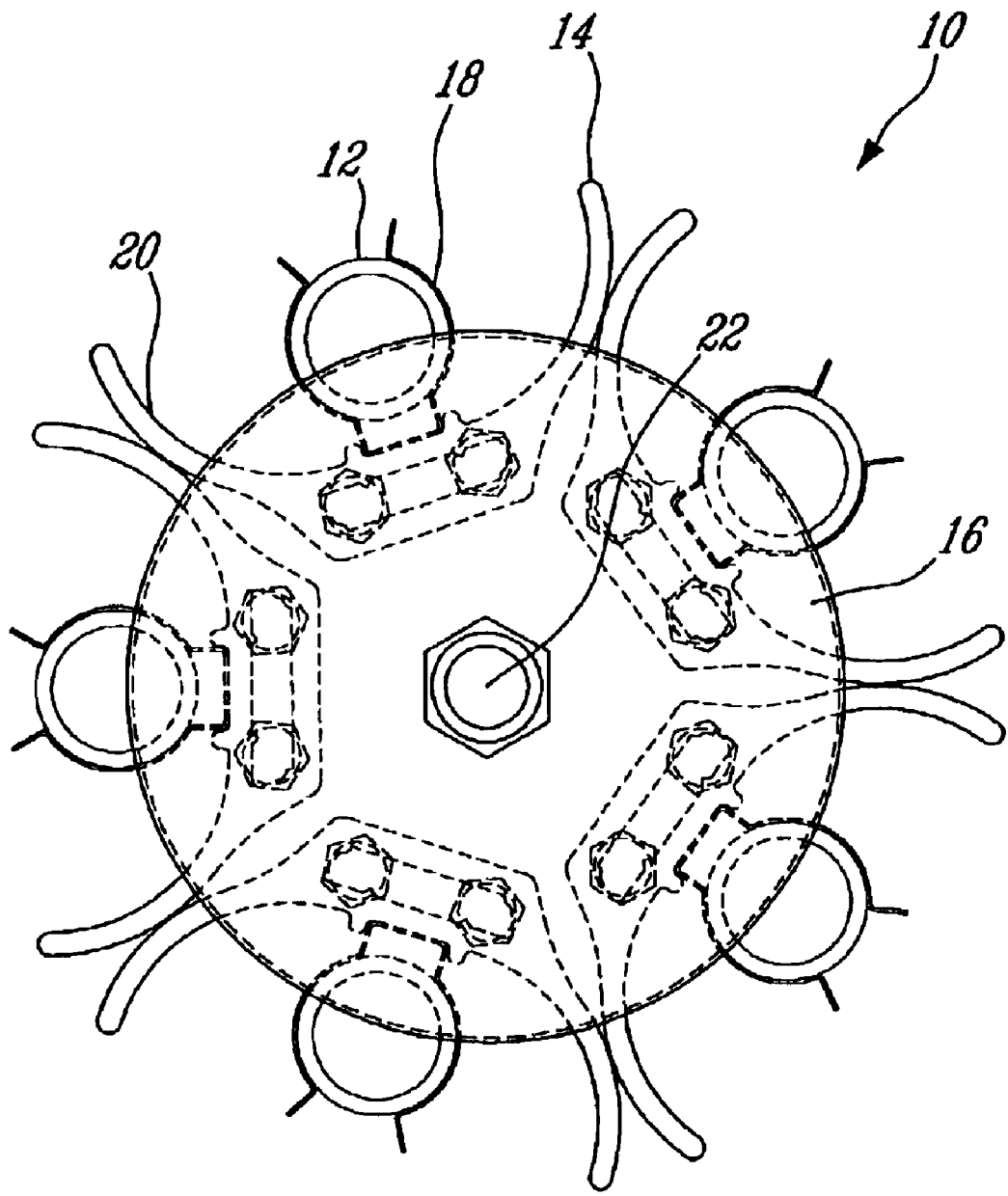
FIG. 2 is an end view of the air purifier of FIG. 1.
Figure 3:
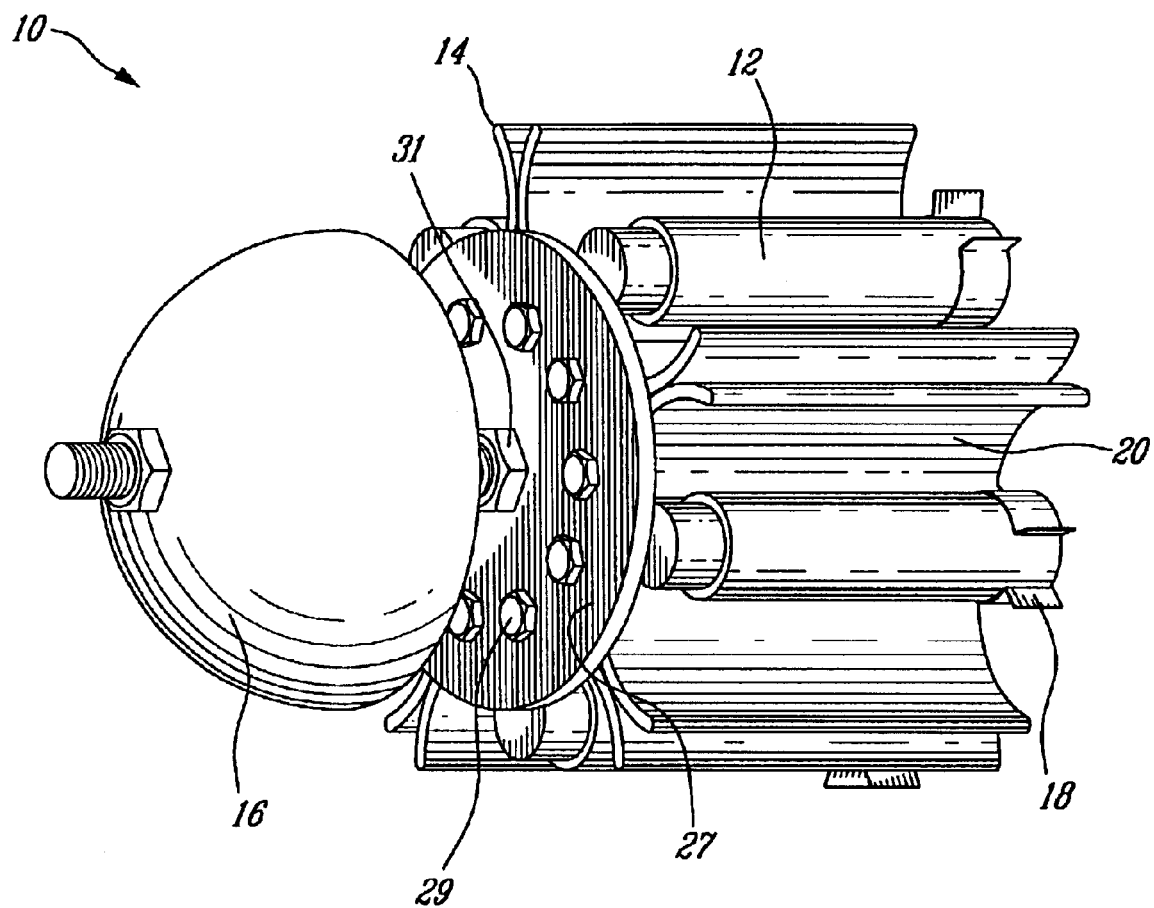
FIG. 3 is a partially exploded view of the proximate end of the air purifier of FIG. 1.

An outwardly projecting air purifier 10 according to a first embodiment of the present invention is illustrated in FIGS. 1 to 3.

Generally stated, the air purifier 10 is designed to be used within air ducts and in other types of ventilation systems supporting a longitudinal airflow and to be positioned along the airflow, such that the airflow meets head-on with a convex shaped deflector element, deflecting the air in the vicinity of the surface of UV lamps which are positioned along the airflow. Therefore, a biological wall is created in the air duct.

As will be described in greater details hereinbelow, the air purifier 10 comprises reflectors having a generally parabolic inner surface, such that essentially all of the UV radiation emitted by UV lamps positioned therein is reflected radially, such that air not directly coming into contact with the lamps is radiated with the maximum possible intensity.

In order to ensure an adequate air purification efficiency, wherever required, several air purifiers in accordance with the present invention can be positioned within the air ducts or other ventilation systems.

Generally stated, the air purifier according to the present invention is an apparatus comprising a plurality of UV lamp assemblies, each including a germicidal lamp removably positioned within a reflector having a generally parabolic inner surface. These lamp assemblies are so positioned that a cylindrical array of UV lamp assemblies is obtained. A convex shaped deflector element is positioned at the proximate, or upstream, end of the air purifier. The apparatus is positioned against the airflow, such that the airflow meets head-on with the convex shaped deflector element, deflecting the air over the surface of the UV lamps, hence subjecting the air to UV radiation.

One skilled in the art will appreciate that an oxydizing/germicidal lamp could also be used in the UV lamp assemblies.

Generally, a preferred position of the air purifier in a ventilation system is before the HVAC coil, after the filter, on the return side of the coil. In this preferred position, both the coil and the drainpan will be contaminant free. The fact that the air moves slower on the return side of the coil than on the supply side, means that the efficiency of the air purifier is higher when mounted in this position, and requires less units for the same killing percentage than if the installation is on the supply side of the coil. In most existing applications, the preferred mounting is not practical, as there is not enough room between the filter and the coil to do the installation. In these instances, the air purifier is mounted in the supply duct after the coil.

Turning now more specifically to the appended FIGS. 1 to 3, an air purifier 10 comprising a cylindrical array of five UV lamp assemblies, each comprising a UV lamp 12 mounted to a respective reflector 14 via two or more securing clamps 18 will be described.

As can be better seen from FIG. 2, each reflector 14 comprises a generally parabolic inner surface 20, reflecting the UV radiation emitted by the lamp 12 in an outward, radial, direction. The shape of the inner surface 20 and the position of the lamp 12 with respect to the inner surface 20 are such that essentially all of the radiation is reflected outward. As will be readily understood by one skilled in the art, the reflector 14 and/or its inner surface 20, is advantageously made of a material that adequately reflects UV radiation such as, for example, aluminum.

Returning to FIG. 1, the five UV lamp assemblies forming the cylindrical array are mounted to a support 22, having a proximate end 24 and a distal end 26, via mounting plates 27 and 28 (see FIGS. 1 and 3) and mounting fasteners 29 (see FIG. 3). More specifically, the mounting plates 27 and 28 are mounted to the support 22 via fasteners 31 (FIG. 3) and the lamp assemblies are mounted to the mounting plates 27 and 28 via the above-mentioned fasteners 29.

The convex shaped deflector element 16 is mounted to the proximate end 24 of the support 22, such that when the air purifier 10 is positioned within the air ducts or other ventilation system, opposite the airflow, the airflow meets head-on therewith and is deflected over the surface of the lamps 12 and continues to flow along the length of the air purifier 10, as will be discussed hereinbelow.

Figure 4:
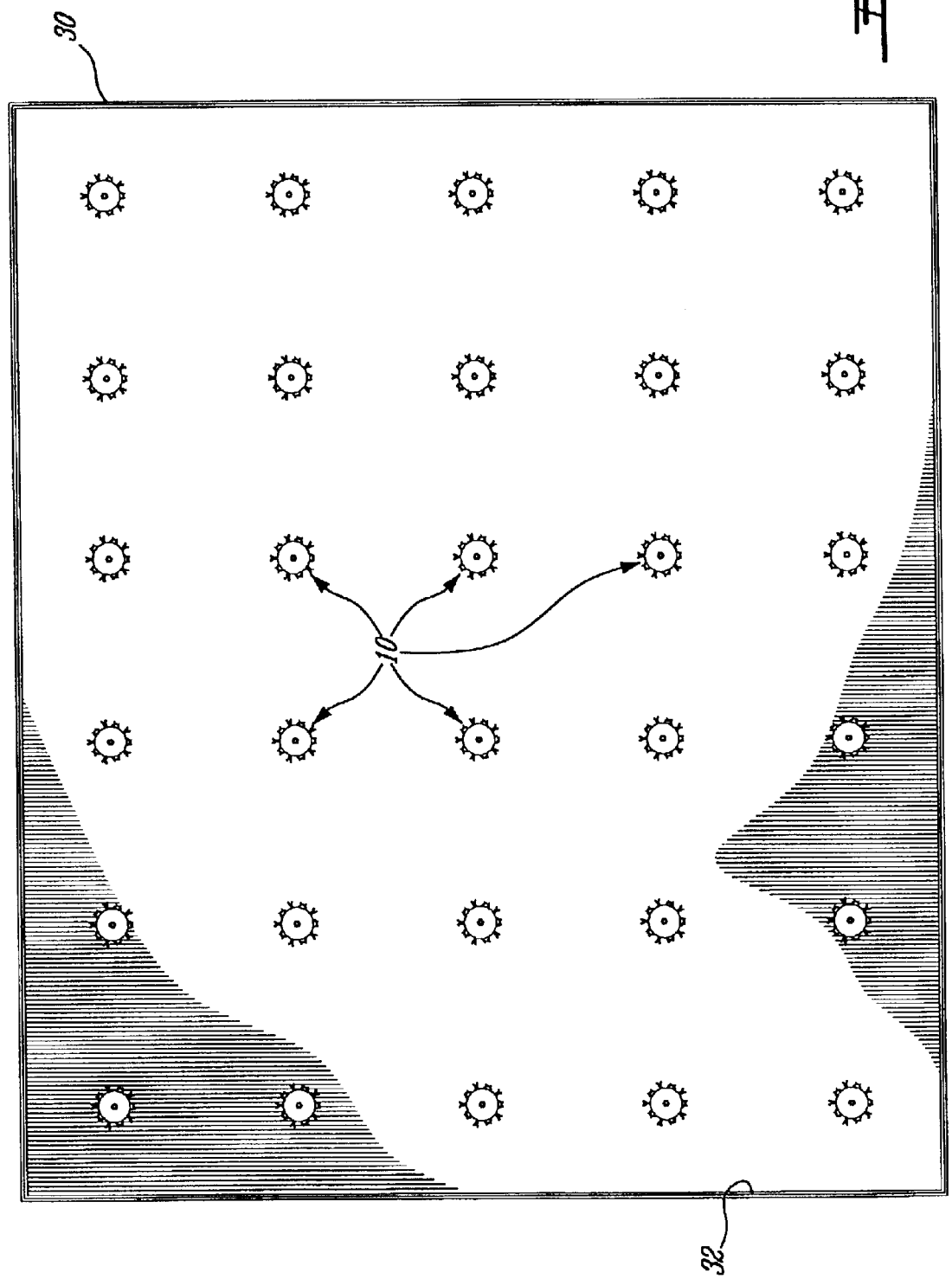
FIG. 4 is a cross-sectional view of an air duct in the direction of the airflow and illustrating a series of air purifier as illustrated in FIG. 1.
Figure 5:
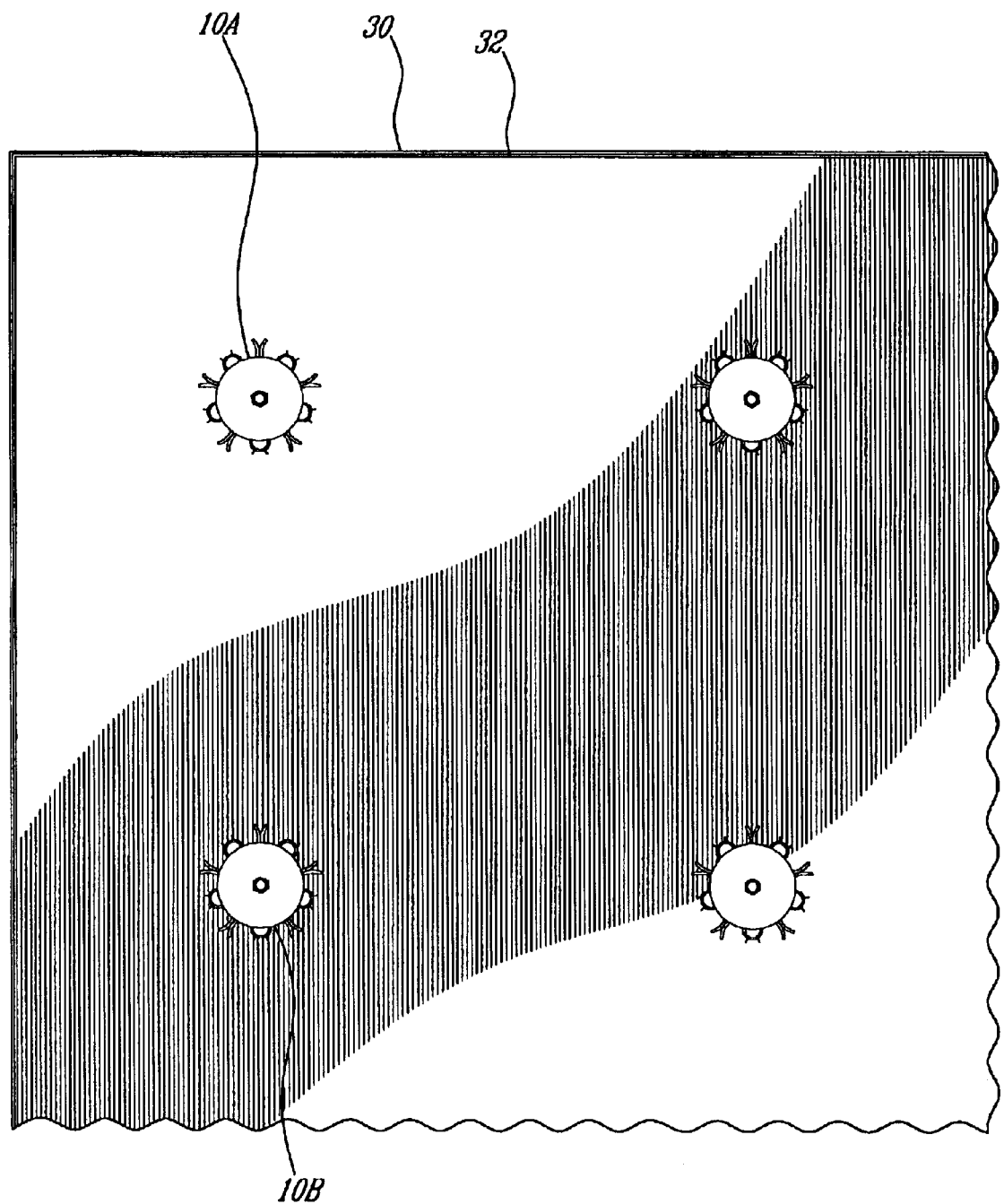
FIG. 5 is an enlarged portion of FIG. 3.

FIG. 4 is illustrative of a cross-sectional view of an air duct 30 or other ventilation system comprising a series of air purifier 10. An enlarged portion of this cross-sectional view is illustrated in FIG. 5. As can be appreciated by one skilled in the art, the internal surface of the duct 30 is covered with a material that adequately reflects UV radiation such as, for example a layer of aluminum 32.

Not shown in these figures is the frame required to maintain the air purifiers 10 in their intended positions. It is believed that one skilled in the art is in a position to design such a frame.

As can be seen from FIG. 5, it will be understood by one skilled in the art that the distance between adjacent air purifiers 10A and 10B may be twice the distance between the air purifier 10A and the inside surface of the duct 30 while maintaining an essentially constant UV radiation across the entire cross-section of the duct 30.

It will also be understood by one skilled in the art that the length and number of required air purifiers 10, as well as the distance separating two adjacent air purifiers 10, depend on many factors such as, for example, the duct cross-section, the airflow speed, the expected level of contaminants, the expected percentage of destruction of the contaminant and the expected nature of the contaminants. It is also to be noted that if the required length of UV lamps is greater than the lamps available, two or more air purifiers may be provided end to end.

It will be understood by one skilled in the art that the reflector and/or its inner surface can be made of extruded aluminum, or any other material that would adequately reflect the incident radiation thereon in a generally radial direction.

The air purifier, in accordance with an embodiment of the present invention, dramatically improves the air quality, more specifically the indoor air quality of buildings, by efficiently purifying and decontaminating the air of many harmful contaminants, whether from biological or other origin. The generally parabolic design of the inner surface 20 of the reflector 14 ensures that essentially all of the emitted UV radiation produced by the lamps is projected in an outward, radial, direction ensuring higher amounts of ultraviolet light traversing the air. This allows for the effective radiation of air not directly deflected by the deflector element.

Additionally, the convex design of the deflector element 16, is both non-obtrusive to the airflow, and also ensures that the air is deflected in the vicinity of the surface of the lamps and continues to flow along the length of the air purifier for an improved efficiency of the assembly.

Figure 6:
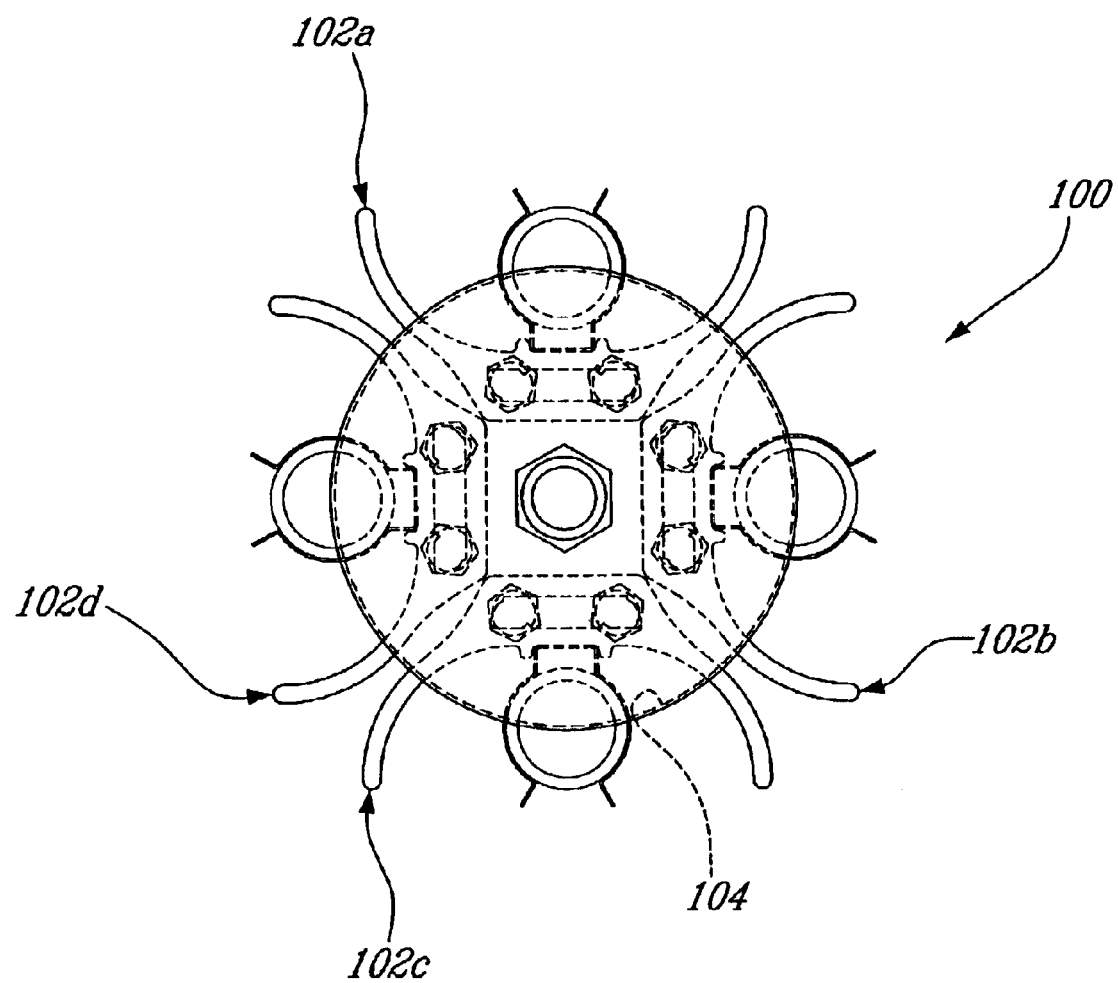
FIG. 6 is an end view similar to FIG. 2 but illustrating an outwardly projecting air purifier according to a second embodiment of the present invention.

Turning briefly to FIG. 6 of the appended drawings, an air purifier 100 according to a second embodiment of the present invention will be described. The air purifier 100 is very similar to the air purifier 10 illustrated in FIGS. 1 to 5 but includes only four UV lamp assemblies 102a–102d mounted to slightly smaller mounting plates 104 (only one shown). One skilled in the art will understand that the number of UV lamp assemblies forming the air purifier is not critical to the operation of the air purifier and is chosen according to the application foreseen for the air purifier.

Turning now to FIG. 7 of the appended drawings, an outwardly projecting air purifier 200 according to a third embodiment of the present invention will be briefly described. Since the outwardly projecting air purifier 200 is very similar to the outwardly projecting air purifier 10 illustrated in FIGS. 1 to 3, only the differences between these outwardly projecting air purifiers will be described hereinbelow.

The main difference between the air purifier 200 and the air purifier 10 of FIGS. 1 to 3 is concerned with filler pieces 202a–202e positioned between adjacent UV lamp assemblies. The purpose of these filler pieces is to prevent air from going between adjacent UV lamp assemblies to thereby allow a portion of the air to avoid being irradiated by the lamps.

As is apparent from FIG. 7, the filler pieces 202a–202e are so shaped that they adequately cover the free space between adjacent UV lamp assemblies.

The filler pieces 202a–202e could be made of extruded aluminum, for example. Of course, other materials and/or method of manufacture could be used.

It is also to be noted that the length of the filler pieces can be equivalent to the length of the UV lamp assemblies, but could also be significantly smaller. In the latter case, the filler pieces would advantageously be positioned near the convex shaped deflector element 16 (not shown in this Figure) to deflect air out of the free space between the adjacent UV lamp assemblies.

The operation of the outwardly projecting air purifier 200 is as described hereinabove with respect to the air purifier 10.

Finally, turning to FIG. 8 of the appended drawings, an outwardly projecting air purifier 300 according to a fourth embodiment of the present invention will be described. Again, only the differences between the outwardly projecting air purifier 300 and the other outwardly projecting air purifiers described hereinabove will be described.

The main difference between the air purifier 300 and the other air purifiers described herein is concerned with the reflectors 302a–302e having an outer surface 304 that is generally flat and that is designed to mate with the outer surface of an adjacent reflector to yield the same result as the filler pieces of FIG. 7.

One will also understand that this mating of the external surfaces of the reflectors 302 makes it possible to forego the use of the central rod 22 and of the mounting plates 27 and 28 by interconnecting the reflectors via fasteners 306. Of course, if this approach is taken, the deflector 308 is not provided with a central aperture but is directly mounted to the reflectors 304 via brackets 310 so configured and shaped as to interconnect the inner concave surface of the deflector to the inner surface of the reflectors. Of course, an aperture could be provided into the deflector should electrical wires have to be passed therethrough.

As will be understood to one skilled in the art, the length of the UV lamp assemblies described hereinabove and illustrated in FIGS. 1 to 6 varies depending on the application intended for the air purifier. For example, 17 inches (about 43 cm) long lamps could be used in a residential setting and 40, 50 or 60 inches (1.02 m, 1.27 m or 1.52 m) long lamps could be used in a commercial or industrial setting.

Although the present invention has been described hereinabove by way of preferred embodiments thereof, it can be modified, without departing from the spirit and nature of the subject invention as defined in the appended claims.

What is claimed is:

1. An outwardly projecting air purifier to be used in an air duct supporting a longitudinal airflow and comprising:
    a support to be positioned within the air duct;
    a plurality of UV lamp assemblies longitudinally mounted to said support; each of said UV lamp assemblies including a reflector having a generally parabolic inner surface and a UV lamp so mounted to said reflector that said generally parabolic inner surface reflects UV radiation emitted by said UV lamp in a radial direction; and
    a convex deflector element so mounted to said support that the airflow is deflected over said UV lamp assemblies.

2. An outwardly projecting air purifier as defined in claim 1, wherein said UV lamp assemblies are mounted to said support via first and second mounting plates.

3. An outwardly projecting air purifier as defined in claim 2, wherein said deflector is secured to said first mounting plate.

4. An outwardly projecting air purifier as defined in claim 3, wherein said deflector is so shaped as to cover said first mounting plate.

5. An outwardly projecting air purifier as defined in claim 1, wherein said UV lamp is secured to said reflector using clamps secured to said inner surface of said reflector.

6. An outwardly projecting air purifier as defined in claim 5, wherein said UV lamp is removably secured to said clamps.

7. An outwardly projecting air purifier as defined in claim 1 wherein said UV lamp is a germicidal lamp.

8. An outwardly projecting air purifier as defined in claim 1 wherein said UV lamp is an oxydizing and germicidal lamp.

9. An outwardly projecting air purifier as defined in claim 1, wherein said plurality of UV lamp assemblies are so positioned as to form a cylindrical array.

10. An outwardly projecting air purifier as defined in claim 1, wherein said reflector comprises aluminum.

11. An outwardly projecting air purifier as defined in claim 10, wherein said reflector comprises extruded aluminum.

12. An outwardly projecting air purifier as defined in claim 10, wherein said generally parabolic inner surface comprises aluminum.

13. An outwardly projecting air purifier as defined in claim 1, wherein said support comprises a threaded rod.

14. An outwardly projecting air purifier as defined in claim 1, wherein said plurality of UV lamp assemblies consists of five UV lamp assemblies.

15. An outwardly projecting air purifier as defined in claim 1, further comprising a plurality of filler pieces so mounted between adjacent reflectors as to prevent air from entering a free space present between adjacent reflectors.

16. An outwardly projecting air purifier to be positioned longitudinally within an air duct supporting an airflow comprising:
    a support;
    a convex shaped deflector element so mounted to said support as to be located upstream with respect to the airflow;
    at least two reflectors having a generally parabolic inner surface mounted to said support; and
    at least two UV lamps each being so mounted to a corresponding reflector that UV radiation emitted by said lamps is reflected in a radial direction;
wherein each of said at least two reflectors is so mounted to said support that airflow is deflected by said convex shaped deflector element over said UV lamps.

17. An outwardly projecting air purifier as defined in claim 16, wherein said reflectors are mounted to said support via first and second mounting plates.

18. An outwardly projecting air purifier as defined in claim 17, wherein said deflector is secured to said first mounting plate.

19. An outwardly projecting air purifier as defined in claim 18, wherein said deflector is so shaped as to cover said first mounting plate.

20. An outwardly projecting air purifier as defined in claim 16, wherein said UV lamps are secured to said reflectors using clamps secured to said inner surface of said reflectors.

21. An outwardly projecting air purifier as defined in claim 20, wherein said UV lamps are removably secured to said clamps.

22. An outwardly projecting air purifier as defined in claim 16, wherein said UV lamps are germicidal.

23. An outwardly projecting air purifier as defined in claim 16, wherein said UV lamps are oxydizing and germicidal.

24. An outwardly projecting air purifier as defined in claim 16, wherein said at least two reflectors includes at least three reflectors that are so positioned as to form a cylindrical array.

25. An outwardly projecting air purifier as defined in claim 16, wherein said reflector comprises aluminum.

26. An outwardly projecting air purifier as defined in claim 25, wherein said reflector comprises extruded aluminum.

27. An outwardly projecting air purifier as defined in claim 25, wherein said generally parabolic inner surface comprises aluminum.

28. An outwardly projecting air purifier as defined in claim 16, wherein said support comprises a threaded rod.

29. An outwardly projecting air purifier as defined in claim 16, further comprising a plurality of filler pieces so mounted between adjacent reflectors as to prevent air from entering a free space present between adjacent reflectors.

30. An outwardly projecting air purifier to be used in an air duct supporting a longitudinal airflow and comprising:
- a plurality of adjacently interconnected UV lamp assemblies each including:
  - a reflector having a generally parabolic inner surface and an outer surface so configured as to be interconnectable with the outer surface of a reflector of an adjacent UV lamp assembly; and
  - a UV lamp so mounted to said reflector that said generally parabolic inner surface reflects UV radiation emitted by said UV lamp in a radial direction;
- a convex deflector element so mounted to said reflectors that the airflow is deflected over said UV lamp assemblies.

\* \* \* \* \*